US012343668B2

(12) United States Patent
Schowalter et al.

(10) Patent No.: US 12,343,668 B2
(45) Date of Patent: Jul. 1, 2025

(54) AIR DISINFECTION CHAMBER

(71) Applicant: Crystal IS, Inc., Green Island, NY (US)

(72) Inventors: Leo J. Schowalter, Latham, NY (US); James Davis, Green Island, NY (US)

(73) Assignee: Crystal IS, Inc., Green Island, NY (US)

( * ) Notice: Subject to any disclaimer, the term of this patent is extended or adjusted under 35 U.S.C. 154(b) by 662 days.

(21) Appl. No.: 17/508,425

(22) Filed: Oct. 22, 2021

(65) Prior Publication Data

US 2022/0040365 A1 Feb. 10, 2022

Related U.S. Application Data

(63) Continuation-in-part of application No. 17/115,737, filed on Dec. 8, 2020, now Pat. No. 11,440,818, which is a continuation-in-part of application No. 16/855,939, filed on Apr. 22, 2020, now Pat. No. 11,279,632.

(60) Provisional application No. 63/138,121, filed on Jan. 15, 2021, provisional application No. 63/114,354, filed on Nov. 16, 2020, provisional application No. 62/836,793, filed on Apr. 22, 2019.

(51) Int. Cl.
*B01D 53/02* (2006.01)
*A61L 9/20* (2006.01)
*B01D 46/00* (2022.01)

(52) U.S. Cl.
CPC ............ *B01D 46/0028* (2013.01); *A61L 9/20* (2013.01); *A61L 2209/12* (2013.01); *A61L 2209/14* (2013.01); *B01D 46/0005* (2013.01); *B01D 2279/50* (2013.01)

(58) Field of Classification Search
CPC .... A61L 2209/12; A61L 2209/14; A61L 9/20; B01D 2279/50; B01D 46/0005; B01D 46/0028; C02F 1/001; C02F 1/325; C02F 2201/3222; C02F 2201/3227; C02F 2201/3228; C02F 2209/40; C02F 2303/04; C02F 2307/06
See application file for complete search history.

(56) References Cited

U.S. PATENT DOCUMENTS

| 4,111,538 A | 9/1978 | Sheridon |
| 6,354,062 B1 * | 3/2002 | Haughton ............. B65B 61/186 53/410 |

(Continued)

FOREIGN PATENT DOCUMENTS

| WO | 2005011753 A1 | 2/2005 |
| WO | 2010071814 A1 | 6/2010 |
| WO | 2019056137 A1 | 3/2019 |

*Primary Examiner* — Christopher P Jones
(74) *Attorney, Agent, or Firm* — Nutter McClennen & Fish LLP (57) ABSTRACT

A system disinfects air. The system includes an elongated chamber having an inlet configured for air to flow into the chamber. The chamber also has an outlet configured for air to flow out of the chamber, and a sidewall formed from a material that is at least 90% UVC reflective. The chamber defines a longitudinal axis. A LED is positioned to emit UVC radiation in a direction substantially perpendicular to the longitudinal axis of the chamber. A filter is configured to trap pathogens. The filter is formed of a material that is UVC reflective and UVC transmissive.

20 Claims, 6 Drawing Sheets

(56) References Cited

U.S. PATENT DOCUMENTS

| | | | |
|---|---|---|---|
| 6,365,920 B1 | 4/2002 | Abramov et al. | |
| 6,961,190 B1 | 11/2005 | Tamaoki et al. | |
| 7,832,885 B2 | 11/2010 | Hsiao et al. | |
| 8,962,359 B2 | 2/2015 | Schowalter et al. | |
| 9,938,165 B2 | 4/2018 | Taghipour | |
| 10,074,784 B2 | 9/2018 | Schowalter et al. | |
| 2002/0126468 A1 | 9/2002 | Umemoto et al. | |
| 2004/0175288 A1* | 9/2004 | Horton, III | C03C 25/1061 422/4 |
| 2007/0091633 A1 | 4/2007 | Harrity et al. | |
| 2007/0102280 A1* | 5/2007 | Hunter | B01D 53/007 422/186.3 |
| 2008/0023719 A1 | 1/2008 | Camras et al. | |
| 2009/0072263 A1 | 3/2009 | Paolini et al. | |
| 2009/0084734 A1* | 4/2009 | Yencho | C02F 1/325 210/243 |
| 2009/0133582 A1* | 5/2009 | Snowball | A61L 9/16 96/224 |
| 2010/0025713 A1 | 2/2010 | Tao et al. | |
| 2010/0237254 A1* | 9/2010 | Mason | C02F 1/325 250/435 |
| 2011/0136394 A1 | 6/2011 | Mostoller et al. | |
| 2011/0226966 A1* | 9/2011 | Takahashi | C02F 1/325 250/492.1 |
| 2012/0069564 A1 | 3/2012 | Andrews et al. | |
| 2012/0228236 A1 | 9/2012 | Hawkins, II et al. | |
| 2013/0323128 A1 | 12/2013 | Owen et al. | |
| 2014/0017135 A1* | 1/2014 | Boodaghians | A61L 9/205 422/121 |
| 2015/0231700 A1* | 8/2015 | Karakkunnummal | B22F 5/00 241/293 |
| 2018/0021471 A1* | 1/2018 | Krosney | B01D 53/007 422/4 |
| 2019/0030510 A1 | 1/2019 | Taghipour | |
| 2019/0035992 A1 | 1/2019 | Schowalter et al. | |
| 2019/0062180 A1 | 2/2019 | Taghipour | |
| 2020/0206374 A1* | 7/2020 | Cordoba | C09D 5/1618 |
| 2020/0392019 A1 | 12/2020 | Benzerrouk | |

* cited by examiner

FIG. 5

AIR DISINFECTION CHAMBER

PRIORITY

This patent application claims priority from provisional U.S. patent application No. 63/114,354, filed Nov. 16, 2020, entitled, "UV LED AIR DISINFECTION SYSTEM WITH HIGH REFLECTIVITY," and naming Leo Schowalter and James Davis as inventors, the disclosure of which is incorporated herein, in its entirety, by reference.

This patent application claims priority from provisional U.S. patent application No. 63/138,121, filed Jan. 15, 2021, entitled, "UVC DURABLE FILTER," and naming Christopher Scully as inventor, the disclosure of which is incorporated herein, in its entirety, by reference.

This patent application is a continuation-in-part of U.S. patent application Ser. No. 17/115,737, filed Dec. 8, 2020, which is a continuation-in-part of U.S. patent application Ser. No. 16/855,939, filed Apr. 22, 2020, which claims priority from provisional U.S. patent application No. 62/836,793, filed on Apr. 22, 2019, all of which are entitled "FLUID TREATMENT REACTOR" and name Leo Schowalter, Rajul Randive, and Steven Berger as inventors, the disclosures all of which are incorporated herein, in their entireties, by reference.

FIELD OF THE INVENTION

Illustrative embodiments of the invention generally relate to treating fluids by UV disinfection and, more particularly, illustrative embodiments relate to a disinfection chamber having an elongated path length for disinfection of air by UVC.

BACKGROUND OF THE INVENTION

UV-C light penetrates the cells of microorganisms and disrupt the structure of their DNA and RNA. This disruption prevents the microorganism from surviving and/or reproducing, rendering it inactive and no longer pathogenic.

SUMMARY OF VARIOUS EMBODIMENTS

In accordance with one embodiment of the invention, a system disinfects air. An elongated chamber has an inlet configured for air to flow into the chamber. The chamber also has an outlet configured for air to flow out of the chamber, and a sidewall formed from a material that is at least 90% UVC reflective. The chamber defines a longitudinal axis. A LED is positioned to emit UVC radiation in a direction substantially perpendicular to the longitudinal axis of the chamber. A filter is configured to trap pathogens. The filter is formed of a material that is UVC reflective and UVC transmissive.

Among other shapes, the chamber may be substantially cylindrical. The chamber may have a length of between about 0.5 meters to about 5 meters, preferably about 1 meter.

In various embodiments, the filter is positioned immediately adjacent to the inlet. The system may also include a second filter in the chamber. In some embodiments, an LED may be embedded in the filter. Additionally, or alternatively, an LED may be positioned to disinfect the filter (e.g. the LED is positioned to emit light substantially towards the filter). The system may include a plurality of LEDs positioned to emit UVC radiation in a direction substantially perpendicular to the longitudinal axis. Preferably, the LEDs may be positioned within 25% and 75% of the length of the chamber. A fluence rate within the chamber may be greater than about 1 mJ/cm$^2$.

In accordance with another embodiment, a method provides a sheet of UVC reflective material. Apertures are formed in the UVC reflective material. The apertures are configured to allow UVC radiation to pass therethrough. A respective LED is positioned in respective aperture. The sheet is formed into a cylindrical shape that defines a chamber.

The method may also position a UVC reflective and UVC transmissive filter in the chamber. The filter may be positioned adjacent to an inlet of the chamber. The filter and/or the sheet may be formed from PTFE.

The method also flows air through the chamber. In some embodiments, a fan upstream of the chamber may be used to increase airflow into the chamber. The method emits radiation into the chamber from at least one LED. An LED is positioned to emit radiation towards the filter. In some embodiments, optical coupler is applied to the respective LED.

In some embodiments, the chamber is fluidly coupled with an environmental control system of an aircraft.

In accordance with another embodiment, a method forms a chamber having a substantially cylindrical shape. The chamber has a length of greater than 0.5 meters, and has a sidewall including a UVC reflective material between an inlet and an outlet. A plurality of UVC LEDs are positioned facing the sidewall of the chamber. A UVC durable and UVC transmissive filter is coupled to the inlet. The UVC LEDs are configured to disinfect air that flows through the chamber and the filter.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, air is efficiently disinfected by ultraviolet light as it flows through an elongated disinfection reactor. The air enters a chamber of the reactor through an inlet and exits the chamber through an outlet. The sidewall of the chamber (or sidewalls, depending on the cross-sectional shape of the chamber) contain one or more LEDs configured to emit at least a portion of light in the wavelength range of 200 nm to 280 nm (i.e., in the UVC range). Furthermore, the sidewall is formed from a material that is highly reflective to UVC, and preferably, diffusively reflective to UVC.

A filter is configured to trap aerosol pathogens of various sizes. The filter may be positioned within the chamber adjacent to the inlet and/or the outlet. The filter is also preferably UVC transmissive and UVC reflective to allow for efficient disinfection of pathogens trapped in the filter. Details of illustrative embodiments are discussed below.

Figure 1:
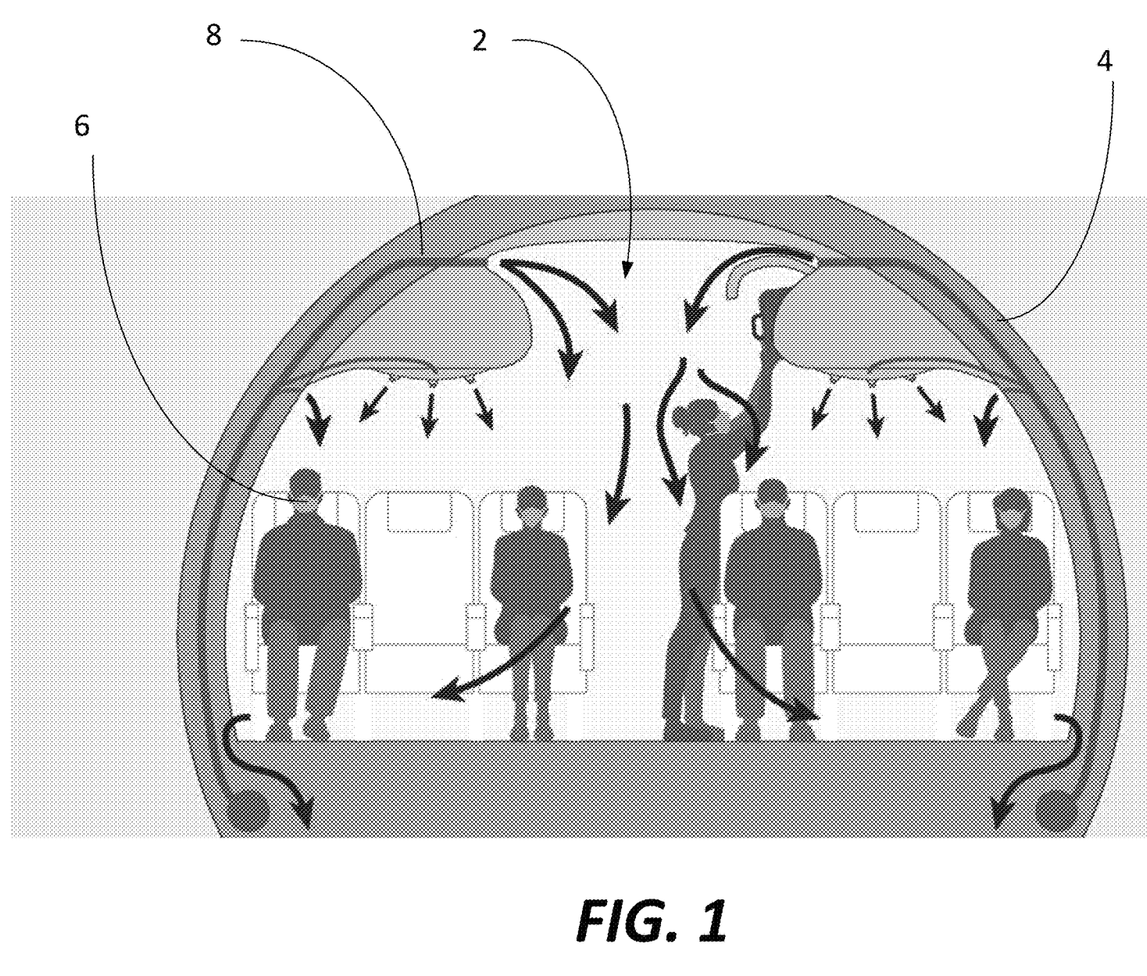
FIG. 1 schematically shows a cabin of a commercial jet aircraft in accordance with illustrative embodiments of the invention.

FIG. 1 schematically shows a cabin 2 of a commercial jet aircraft 4 in accordance with illustrative embodiments of the invention. Given the current outbreak of Coronavirus Disease 2019 (COVID-19) caused by the novel coronavirus SARS-CoV-2, there is renewed interest in reducing risk of infection in enclosed spaces. General safety recommendations include wearing masks 6, such as cotton masks, disposable masks, N95 masks, and/or elastomeric masks. However, masks 6 work with varying degrees of efficiency. For example, N95 masks 6 capture about 95% of particles that are 0.3 microns or greater. Even so, masks 6 are generally not as efficient as an air filtration system of the aircraft 4.

The air filtration system assists with refreshing air in the cabin 2. Air volume in the cabin 2 of a commercial aircraft 4 is generally refreshed every two to four minutes. For example, as shown in FIG. 1, air 8 flows into the cabin 2 vertically—it enters from overhead vents 10 and is sent downward, exiting at floor level. After the air 8 leaves the cabin 2, about half is discharged outside the aircraft 4 (depending on the make and model), and the rest is recirculated throughout the cabin 2. Fresh air 8 is also brought into the aircraft 4 and circulated around the cabin 2.

Generally, the recirculated air 8 passes through the air filtration system, which frequently includes a High Efficiency Particulate Air (HEPA) filter. HEPA filters are about 99.7% effective at capturing microbes, dust, and particulates down to 0.3 microns. HEPA filters include a mix of filaments and fibers that carry a static charge that attracts various microbes and particles. As the particles travel through the air filtration system, they are captured and retained within the filter.

Over time, with enough volume or use, pathogens eventually separate and penetrate the filter due to their sub-micron size. The SARS-CoV-2 virus is approximately 0.125 micron or 125 nanometers in diameter. However, it often travels in biological aerosols (e.g., from coughing or sneezing) that range in size from 0.5 micron-3.0 micron. These aerosols are largely captured by the filter, but it is possible that the virus/pathogen may separate from the aerosol if, for example, the aerosol evaporates.

As HEPA filters (and other filters) become clogged with moisture, aerosols eventually evaporate or push through the filter. Therefore, illustrative embodiments disinfect the filter as the pathogen is trapped thereon. However, filters cannot easily be decontaminated with UVC, as they are typically opaque to UVC, and also vulnerable to degradation by UVC. Thus, traditional filters (whether HEPA filters or mask filters) provide areas where the pathogens are protected from UVC disinfection. Illustrative embodiments provide a system including a chamber with a filter that may be reliably and durably disinfected using UVC radiation.

Figure 2:
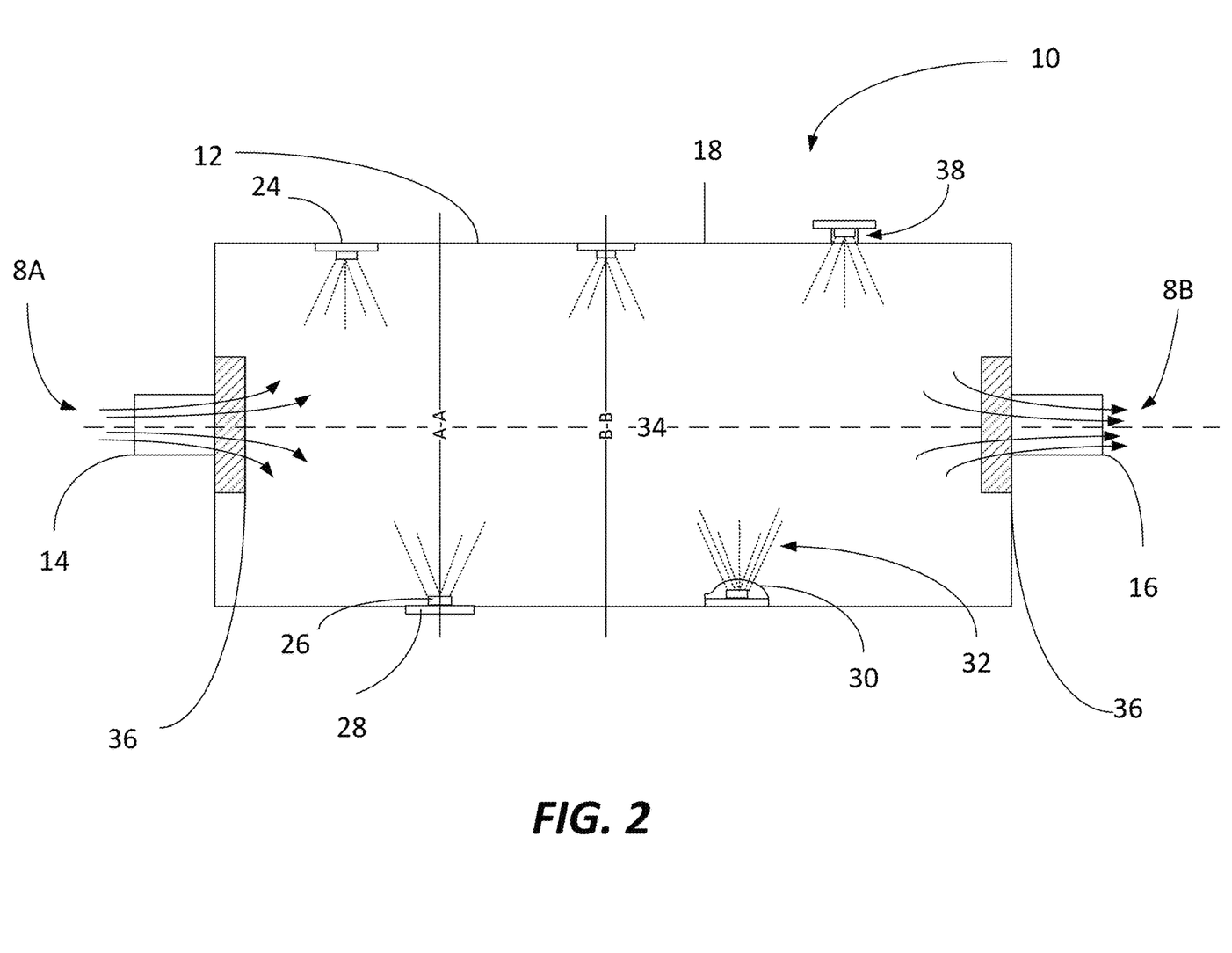
FIG. 2 schematically shows a UVC photoreactor in accordance with illustrative embodiments of the invention.

FIG. 2 schematically shows a UVC photoreactor 10 in accordance with illustrative embodiments of the invention. Contaminated air 8A enters the chamber 12 of the reactor 10 through an inlet 14. The contaminated air 8A is disinfected (partially or completely) in the chamber 12 and exits as disinfected air 8B from an outlet 16 of the chamber 10. For example, the outlet 16 may be directly in fluid communication with the cabin 2 of the airplane, an automobile, or an elevator. Additionally, the outlet 16 may be upstream of a traditional air filtration system.

The reactor 10 may be used to disinfect large quantities of air, such as the air 8 circulating in the cabin 2. To assist with passing adequate volumes of air 8 in a timely manner, illustrative embodiments may include a fan or a pump (not shown) fluidly coupled, upstream and/or downstream, of the chamber 12.

The reactor 10 includes at least one light-emitting diode 24 (LED 24), preferably a UVC-emitting LED 24, that disinfects the air 8 in the chamber 12. Light-emitting diodes 24 (LEDs 24) that produce UV radiation are becoming more commonly available. As used herein, the term "LED" 24 refers collectively to an LED chip 26 and a package 28 (e.g., on which the chip 26 is mounted). To the inventors' knowledge, there are two types of surface mounted UV LEDs 24. A first type of LED 24 includes the LED chip 26, the package 28 containing the LED chip 26, and a lens (e.g., a quartz window) covering the LED chip 26 within the package. A second type of LED 24 includes an exposed LED chip 26 and a package 28 (e.g., a lidless package) containing the LED chip 26. The second type of LED 24 may be a commercially available device, such as the KLARAN™ UV LED 24, distributed by Crystal IS, Inc. and Asahi Kasei. Furthermore, various embodiments may include an optical coupler 30 configured to increase the effective dosage of radiation 32 emitted by the LED 24. These LEDs 24 and the optical coupler 30 are described in greater detail in copending U.S. application Ser. No. 17/115,737, which is incorporated herein, in its entirety, by reference.

Illustrative embodiments position the LEDs 24 in the chamber 12 such that one or more of the LEDs 24 face a sidewall 18 of the chamber 12 (e.g., light emitting surface of the chip 26 faces perpendicular to a longitudinal axis 34 of the chamber 12), as shown in FIG. 2. By facing the sidewall 18, UVC radiation 32 is substantially directed towards the highly reflective sidewall 18. However, some embodiments may additionally, or alternatively, position LEDs 24 so that they face along the length of the chamber 12 (e.g., facing parallel to the longitudinal axis 34 of the chamber 12). As discussed below, positioning LEDs 24 so that they are facing perpendicular to the longitudinal axis provides a number of advantages when disinfecting air (e.g., particular large volumes of air).

Inside of the chamber 12 are one or more filters 36 configured to trap pathogens of varying sizes. The filter 36 may be positioned immediately adjacent to the inlet 14 and/or the outlet 16. Positioning the filter 36 immediately adjacent to the inlet 14 provides a number of advantages. For example, droplets/aerosols are prevented or inhibited from making it into the chamber 12 where they would otherwise stick to the walls 18 and coat the inside of the chamber 12. Furthermore, the introduction of dust into the chamber 12 is prevented or hindered. Dust undesirably may coat and reduce the reflectivity of the walls 18.

Although FIG. 2 shows the filter 36 immediately adjacent to the inlet 14 and the outlet 16, the filter 36 may be positioned in a variety of ways within the chamber 12. For example, the filter 36 may be substantially perpendicular to the longitudinal axis 34 at any position inside the chamber 12. Preferably, the filter 36 spans the entire diameter/width of the chamber 12, such that there are no zones where air 8 can bypass the filter 36. In various embodiments, the filters 36 are configured to capture particles at least as small as the aerosols that carry the SARS-CoV-2 virus. When pathogens are trapped in the filter, UVC radiation 32 emitted by LEDs 24 inactivates and/or kills the pathogens.

As described above, illustrative embodiments prevent or inhibit droplets/aerosols from making it into the chamber 12 (e.g., as these droplets release virus as the droplets evaporate). It is preferable to kill the virus while it is captured in the filter 36. Therefore, various embodiments may radiate the filters 36 with LEDs 24 (e.g., by direct transmission or indirectly by reflection). In some embodiments, one or more LEDs 24 may be embedded in the filter 36. Some virus may still make it through the filter 36, but the LEDs 24 in the chamber 12 disinfects a large proportion of virus that makes it through the filter and into the chamber 12. To that end, at least some of the LEDs 24 are between filters 36, and/or downstream of the filter 36 nearest the inlet 14. Positioning the LEDs 24 on the sidewall 18 rather than on the end wall 40/entrance also allows the UVC radiation to disinfect pathogens without having to pass radiation through the filter 36.

Typically, UVC LEDs 24 emit a very narrow wavelength band of radiation. Currently available UVC LEDs have peak wavelengths at 214 nm, 265 nm, and 273 nm, among others. One advantage of LEDs 24 over low-pressure mercury lamps is that they contain no mercury. Because LEDs 24 have smaller surface area and higher directionality, they may be considered less effective for germicidal applications.

Illustrative embodiments advantageously form the filter 36 from materials that are both UVC transmissive and UVC diffusively reflective, such as PTFE. The properties of these materials allow smaller-dosage UVC radiation (as compared to mercury lamps of similar size and weight) to spread throughout the filter 36 (e.g., throughout the fibers) thereby inactivating various pathogens trapped in the filter 36. In some embodiments, the filter may be formed from a porous PTFE material that could be made substantially transparent to UVC radiation.

Prior art filters that are not UVC transmissive and/or UVC diffusively reflective may not achieve high levels of pathogen inactivation. The filter 36 may be formed of a material that is UV translucent (e.g., some of the light would transmit through the filter and some would be reflected). For example, forming the filter of a material that is at least partially UVC transmissive allows the UVC radiation to pass through the material of the filter 36. Furthermore, forming the filter of a material 36 that is at least partially UVC diffusively reflective allows the UVC radiation to reach all, or substantially all, of the pathogens trapped in the filter 36. A material having a combination of these features (i.e., UVC transmissive and UVC diffusively reflective) advantageously provides both benefits.

Various embodiments of the filter 36 are described in U.S. patent application No. 63/138,121, which is incorporated herein by reference.

In various embodiments, the chamber 12 is configured to assist with disinfection. For example, the chamber may have an elongated length of about 1 meter. Some embodiments may form the inner walls 18 and/or 40 of the chamber 12 from an inexpensive material that is about 70% reflective to UVC, such as aluminum. Additionally, or alternatively, the walls 18 and/or 40 may be coated with a highly UVC reflective material, such as PTFE.

Some embodiments may include a lower UVC reflective material (e.g., 70% UVC reflective aluminum). This advantageously reduces costs relative to highly UVC reflective material, but require the introduction of a larger fluence of UVC radiation compared to higher UVC reflective material, all else being the same. Therefore, some embodiments may use a mercury lamp to provide large UVC power output. However, UVC lamps suffer from a number of disadvantages. For example, UVC lamps are constantly left on to avoid the stresses of thermal cycling and/or to prevent degradation of the output power of the lamp. However, uninterrupted use of the lamp may waste energy and reduce the useful life of the system. In contrast, the LED 24 can be power cycled, and turned on and off instantly. Furthermore, mercury lamps emit light in 360 degrees and generally are positioned in the center of the chamber 12. Mercury lamps negatively impact the overall average reflectivity in the chamber by undesirably functioning as an absorber in the center of the chamber 12.

Accordingly, illustrative embodiments may use LEDs 24 instead of a mercury lamp, greatly increasing the average reflectivity inside the chamber 12 (i.e., because the mercury lamp is no longer a large absorber). In some embodiments, the reflectivity of the sidewalls 18 of the chamber 12 may be high, such as 90% UVC reflective or higher. The high reflectivity causes the emitted radiation to have a large total path length before absorption (e.g., because of a large number of reflections and because of the low UVC absorption of air). Thus, although the diameter of the chamber 12 is small (e.g., decimeter scale), the total path length of the emitted light is large (e.g., kilometer scale). The high reflectivity of the chamber 12 allows the LEDs 24, which in general have a lower power output than the mercury lamp, to provide up to a 1-log reduction in pathogens. Therefore, the fluence inside the chamber 12 is considerably high despite the relatively low power output of LEDs 24 (as compared to mercury lamps).

Some embodiments may use mercury lamps, however, mercury lamps do not provide for directing light emission in the way LEDs 24 do. It was thought in the art that mercury lamps are preferable over LEDs 24 because LEDs 24 were considered not to be strong enough (i.e., because of the low reflectivity of the walls 18). Therefore, the practice is the art is to aim the light beams parallel to the longitudinal axis 34, as opposed to perpendicular. However, illustrative embodiments advantageously emit light in a direction perpendicular to the longitudinal axis 34. Furthermore, the state of the art using mercury lamps fails to disclose the advantages of a large chamber 12, because the light is not directed (e.g., mercury lamp just scatters), mercury lamps achieve a very low reflectivity.

Furthermore, as compared to water, air has a considerably lower UVC absorption coefficient. As a result, the ultimate path length of UVC within the high reflectivity chamber may be on the scale of kilometers (as opposed to centimeters when disinfecting water). Furthermore, air does not need to achieve the same degree of disinfection in one pass through the chamber as is usually achieved for water. Generally, water disinfection applications seek to achieve about a 3-log reduction in pathogens. In contrast, for air quality applications, a 50% reduction to 90% reduction (1–log) may be achieved for a single pass through the chamber. In contrast to water disinfection applications, the air 8 passes through the filter 36 repeatedly as it is recirculated (as opposed to being drank by a user). Therefore, the air 8 is repeatedly disinfected in the chamber 12. This greatly improves the probabilities of avoiding the spread of disease, as the likelihood of getting sick generally has some proportionality to the size of the virus load.

Figure 3A:
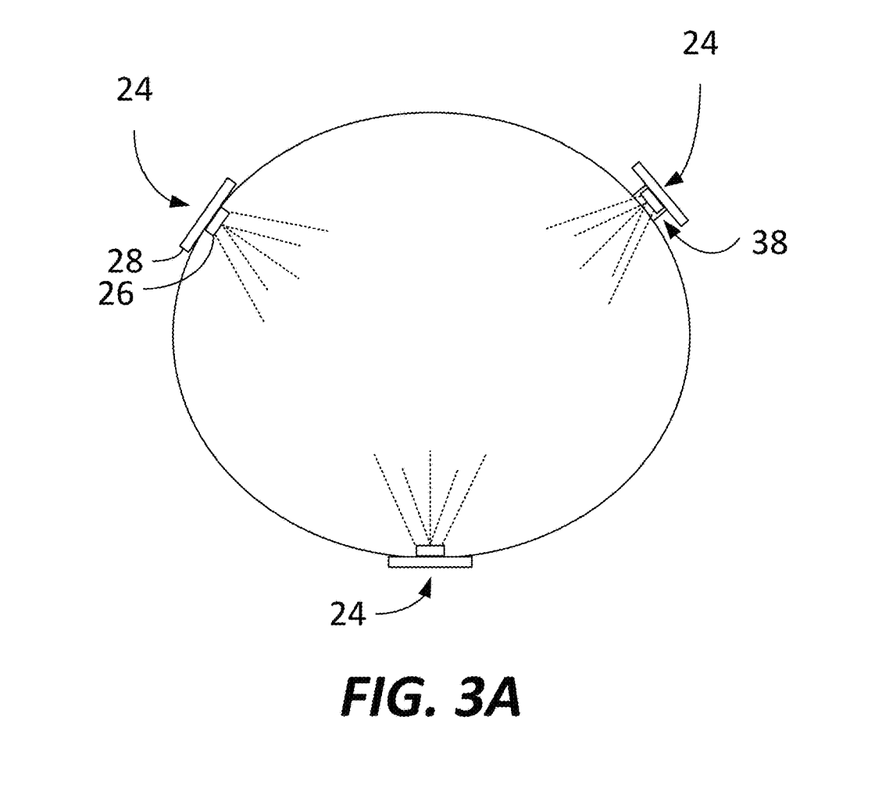
FIG. 3A schematically shows a cross section of the chamber of FIG. 2 along line A-A.

FIG. 3A schematically shows a cross section of the chamber of FIG. 2 along line A-A. Although the cross-section of FIG. 2 shows only a single LED 24 along line A-A, it should be understood that a number of LEDs 24 may be disposed along any given section (as shown in FIG. 3A). For example, the LEDs 24 may be distributed approximately 120 degrees around a circumference of the chamber 12, such that the LEDs are not directly facing each other.

To minimize the non-reflective space taken up by the LED 24, illustrative embodiments may position the LED chip 26 (or a light emitting portion thereof) in the chamber 12, while the larger LED package 28 remains outside of/behind a reflective inner surface of the chamber 12. Some embodiments may completely position the LED 24 outside of the chamber 12 (e.g., by using a light pipe 38 to transit the radiation into the chamber 12). Details of the light pipe 38 and/or arrangements of the light pipe 38 with the LED 24 in accordance with illustrative embodiments of the invention are described in U.S. patent application Ser. No. 16/672,450, which is incorporated herein by reference in its entirety.

Figure 3B:
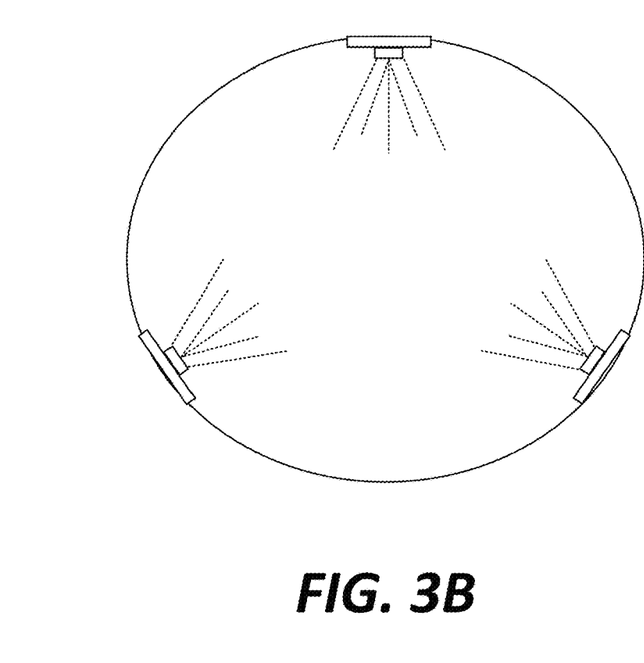
FIG. 3B schematically shows a cross-section of the chamber of FIG. 2 along line B-B.

FIG. 3B schematically shows a cross-section of the chamber of FIG. 2 along line B-B. As shown, in some embodiments, the LEDs chip 26 and package 28 may be inside the chamber 12. However, preferred embodiments have the package 28 outside of the chamber 12, so as to reduce UVC absorption.

Figure 3C:
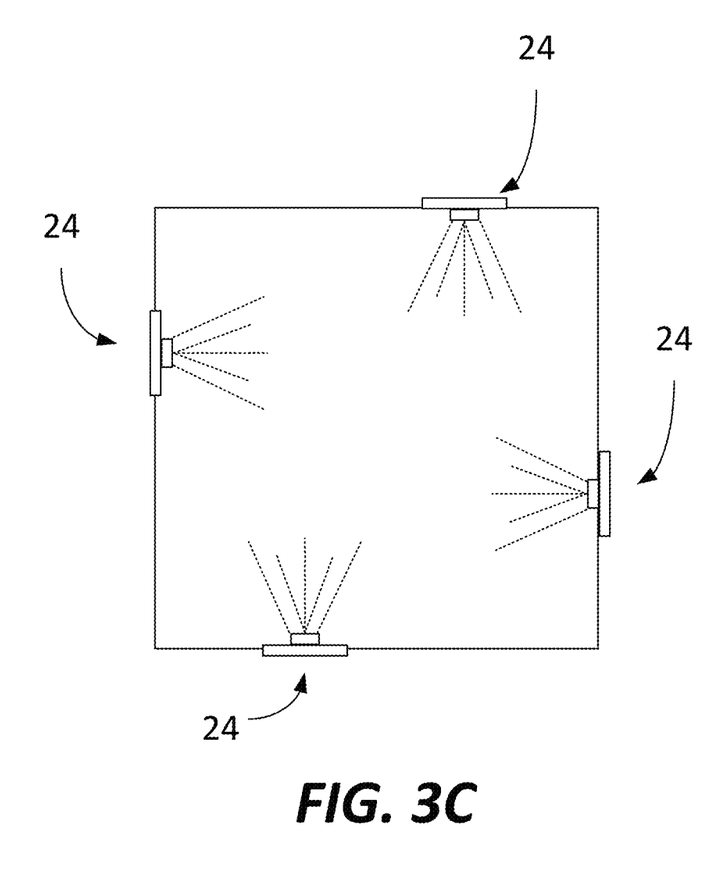
FIG. 3C schematically shows a cross-section of an alternative chamber having a rectangular cross-section in accordance with illustrative embodiments.

FIG. 3C schematically shows a cross-section of an alternative chamber 12 having a rectangular cross-section in accordance with illustrative embodiments. As shown, the LEDs 24 may be distributed so that they do not directly face one another. Thus, the radiation that is absorbed by LEDs 24 (e.g., the package) is relatively small.

Returning to FIG. 2, illustrative embodiments preferably position LEDs towards a middle of the chamber 12 (e.g., with reference to the longitudinal axis 34). Thus, the radiation that is leaking out towards the inlet and the outlet is relatively small. Accordingly, the number of average reflections of omitted light beams are advantageously increased with a smaller output power for the LEDs 24.

Illustrative embodiments thus enable more effective disinfection of air 8 in the chamber 12 using LEDs.

A significant problem with air disinfection is that relatively large volumes of air typically need to be disinfected (e.g., compared, say to water). Another issue is that people need to be shielded from UVC radiation (although the risk of UVC exposure, particularly at short wavelengths, is not as well understood as desired). On the other hand, one significant advantage of air disinfection is the high transparency of air. This means that a relatively small amount of UVC power can disinfect a significantly large volume of air if the effective path length can be made very long. Illustrative embodiments increase the effective path length (i.e., until the UVC is fully absorbed) by facing the LEDs 24 substantially perpendicular to the longitudinal axis 34 of the chamber 12, where they reflect repeatedly. Furthermore, reducing the amount of UVC that is absorbed (e.g., by making the LED 24 aperture small by positioning the package 34 outside of the chamber 12) also increases the average path length of various beam.

For air, we can define an absorption length $\alpha$ which defined such that the irradiance of a columnated beam would be reduced from its initial value:

$e^{-\alpha r}$ after traveling a distance r in the air.

As with the disinfection of fluid, the maximum reduction equivalent dose (RED) that is possible for a given UVC radiation power Pc introduced into the fluid disinfection reactor is:

$$\frac{P_c}{\alpha f}$$

where f is the flow rate of fluid through the reactor.

This result assumes that all the incoming radiation is absorbed by the fluid and that all the fluid that flows through the reactor gets the same dose. It also assumes that the absorption coefficient is dominated by absorption that does not change during exposure to the radiation. This is generally the case in actual situations, except perhaps in very pure fluid or for very high irradiation levels. In actual reactors, the RED is typically much smaller because radiation is absorbed by walls or other elements of the reactor and it is difficult to achieve flow and radiation conditions where all elements of fluid flow get the same dose.

Because the absorption is so small for typical situations with air, the maximum RED in an air disinfection reactor will be dominated by high far the radiation travel before being hitting a wall of the chamber if the chamber walls are all absorbing. Thus, we can write Equation 1:

$$RED \leq \frac{[r]P_c}{f}$$

Where the square brackets [ ] around r are used to represent a mean of the distance the UVC radiation will travel from its source before hitting a wall.

Example 1: suppose we want to disinfect 24 L/s (=24,000 cm$^3$/s) of air flowing through a chamber 12 that is 40 cm long. A collimated beam going down the 40 cm long axis of the chamber 12 has [r]=40 cm. If it is desired to achieve 3 mJ/cm$^2$ fluence (dose) using 265 nm LEDs 24 in a single pass through the chamber 12, then the output power of the LEDs 24 needs to be greater than $P_C$=(3)(24000)/40=1,800 mW=1.8 W. Note that if the reaction chamber 12 is made shorter and/or the radiation is, in fact, also partially absorbed by the sidewalls 18 because the UVC radiation is not completely collimated, the power needed is higher.

It should be noted that the transparency of very clean air is considered to be about 1E-5/cm at 265 nm (data from Caltech PhD thesis, 1950 CaltechETD:etd-08272008-082651.) More typical would still be smaller than 1E-4/cm. Of course, smoke or water droplets could significantly reduce this value, but it is probably still not relevant for path lengths less than 10 m. In addition, scattered light would still contribute to disinfection; only radiation that is actually absorbed in some other photochemical process would be lost.

On the other hand, reflecting walls 18 substantially reduce the UVC power needs. If the "mean" reflectivity of the chamber is [R], then the maximum RED can be calculated as Equation 2:

$$RED \leq \frac{[r]P_c}{f(1-[R])}$$

It is important to recognize that [R] must include the light source itself. Thus, for instance, the chamber walls might be made of a type of PTFE with reflectivity greater that 90% (for this example, assume that the material has a reflectivity of exactly 90%). However, if 10% of the surface area of the reactor chamber is taken up by the UVC light source, then

[R] is only 80% (or 0.8). In this case, 1−[R]=0.2 and the minimum power required to achieve 3 mJ/cm² in one pass through the reactor as discussed in the previous reactor is be reduced from 1.8 W to 0.36 W. If, on the other hand, the area of the radiation source could be reduced to only 1% of the chamber wall 18 surface area, then, 1−[R]=0.11 and the power needed is reduced by a factor 9.1 from 1.8 W to only 0.2 W. Thus, the use of reflective walls with very small radiation sources can be quite effective in reducing the power needed to disinfect air.

Example 2: In illustrative embodiments, Virtek PTFE from Porex is used with a reflectivity of 97% at 265 nm. In this case, one or two UVC LEDs 24 may be used with a very small footprint. Thus, an [R] of 96% is achievable in illustrative embodiments. In this case, consider the chamber 12 to be smaller with an [r] of only 15 cm. To achieve 3 mJ/cm2 per pass at a flow rate of 25 L/s, a minimum power of 200 mW is required.

Example 3: Illustrative embodiments may use polished aluminum with a reflectivity of 70% (e.g., instead of Virtek PTFE in the above example). In this case, again assume 1% of the area is taken up by the LED 24 sources. Thus, [R]=69%. Then, 1−[R]=0.31. In that case, a single pass fluence (dose) of 3 mJ/cm2 will require at least a PC=(3)(25000)/15*(0.31)=1.55 W. This is a significantly large difference.

Illustrative embodiments may position the LEDs 24 so that they are facing along the flow of the air 8 (e.g., substantially parallel to the longitudinal axis 34), or perpendicular to the flow of the air 8 (e.g., substantially perpendicular to the longitudinal axis 34).

The inventors determined that, for non-reflecting walls 18, illustrative embodiments preferably use the shorter distance for [r] in Eq. 1. However, it is difficult to obtain a uniform dose in this case so, without a lot of care, the RED is likely to be significantly lower than the upper limit given in Eq. 1.

The inventors also determined, that for illustrative embodiments with highly reflective walls (e.g., [R] is greater than 90%), [r] is an average of all the different path lengths in the reactor. This average [r] can be hard to calculate if the chamber 12 has a complex shape. However, for a sphere, [r] may be calculated as ⅔ the diameter of the sphere, assuming that all reflections are Lambertian (i.e., the probability that the reflection goes in any particular direction is given by cos θ where θ is the angle from the normal to the surface). For a cylinder, one skilled also should have the capability to make a reasonably close estimate. In this case, the source of the radiation being from the side (belly band) or along the axis so long as the walls of the chamber are highly reflective. One skilled in the art likely would expect that diffuse reflections would make the diameter of the cylinder dominate over the length of the cylinder. When [R] is smaller (say 70%), a proper calculation is more complicated because the number of reflections is rather small. In this case, the original orientation of the source of UVC radiation is likely more important.

It is expected that most of the contribution of the disinfection come from the first 3 or 4 reflections, which may be mostly along the short axis if the LED is oriented perpendicular to the cylinder. On the other hand, if the LED is oriented along the axis of the cylinder, the first pass will be primarily along the long axis of the cylinder. Illustrative embodiments may use a specular reflection to keep most of the radiation directed along the long axis. For specular reflective surfaces, the initial orientation of the radiation is significant. For diffuse reflection, especially with highly reflective material, the orientation of the initial radiation is not as significant.

In various embodiments, the sidewall 18 is diffusively reflective to UVC. The inventors have tested and found that sidewalls 18 that are diffusively reflective to UVC lead to better fluence throughout the chamber 12, and thus, better disinfection. This improved disinfection is further enhanced by having an elongated chamber 12 where the LEDs 24 are oriented perpendicular to the longitudinal axis, rather than parallel as is done in the prior art.

However, the inventors have found that there are certain situations where making the walls 18 specularly reflective to UVC may be advantageous. For example, when the chamber 12 has a long length (e.g., in excess of 2 meters), a specular wall 18 may be advantageous so long as the LEDs 24 are oriented parallel to the longitudinal axis 34. However, if the chamber 12 cannot be made many meters long (e.g., in excess of 2 meters), then diffusive reflection provides improved disinfection.

Prior art known to the inventors for disinfecting air emits light substantially parallel to the longitudinal axis 34. Therefore, the light travels along the length of the chamber 12 before being absorbed or reflected. In contrast, illustrative embodiments bring light in from the side (e.g., by positioning on sidewalls 18) and advantageously allow for the positioning of substantially more LEDs 24 (e.g., than may fit on the endwalls 15). As the chamber 12 is made smaller, the reflectivity of the walls 18 become more important, as the light has less length to travel before hitting a surface and being absorbed and/or reflected. Accordingly, some embodiments may position LEDs 24 to emit light substantially perpendicular to the longitudinal axis 34, and make the sidewalls 18 diffusively reflective to UV (e.g., UVC). Additionally, some embodiments may position LEDs 24 parallel to emit light substantially perpendicular to the longitudinal axis 34, and make the endwall(s) 15 specularly reflective to UV (e.g., UVC). In some embodiments, the length of the chamber 12 may be less than 2 meters.

Figure 4:
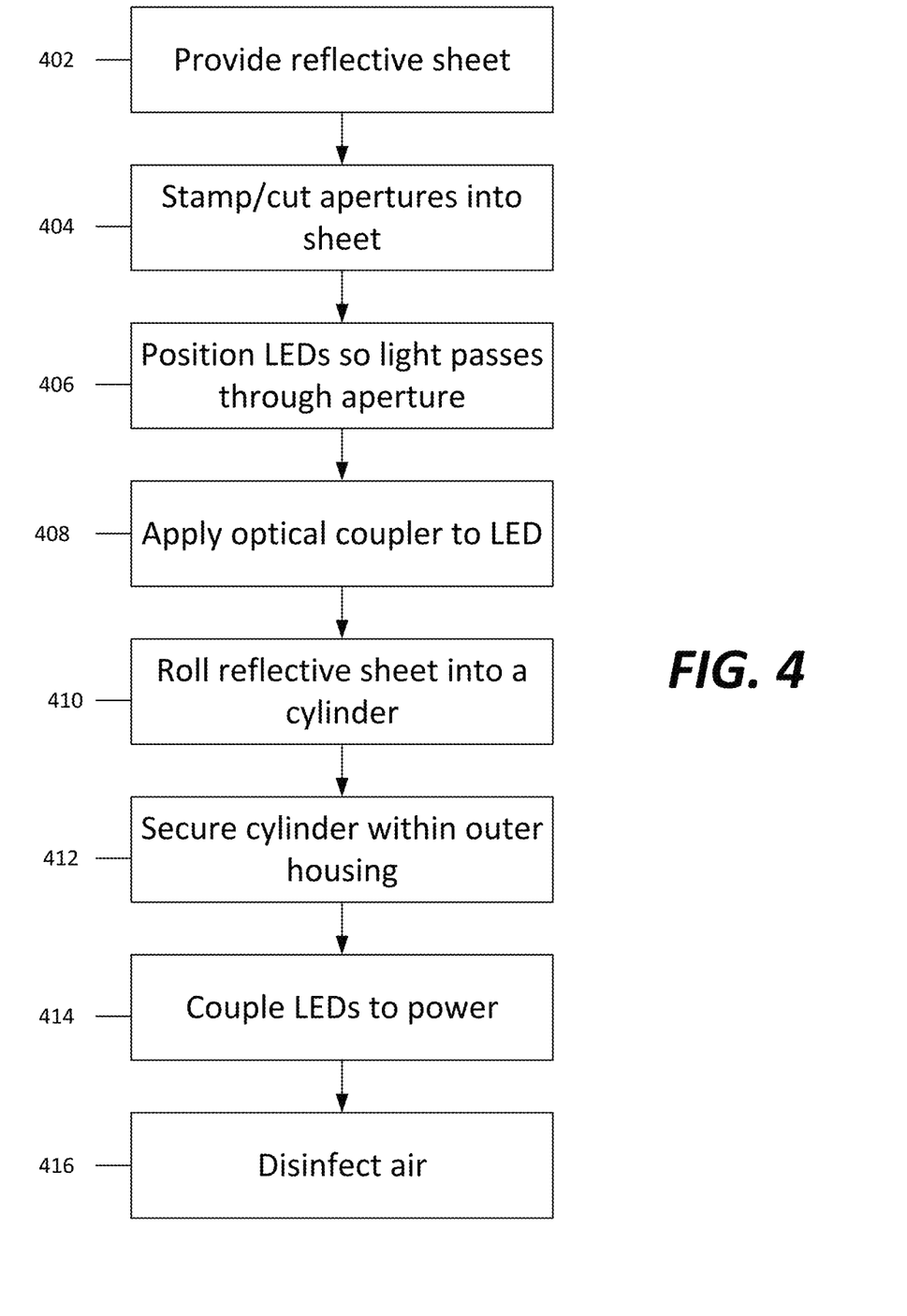
FIG. 4 shows a method of assembling and using a UVC disinfection chamber in accordance with illustrative embodiments of the invention.

FIG. 4 shows a method of assembling and using a UVC disinfection chamber 12 in accordance with illustrative embodiments of the invention. It should be noted that this process is simplified from a longer process that normally would be used to assemble and use a UVC disinfection chamber 12. Accordingly, the process of assembling and using the UVC disinfection chamber 12 likely has many steps that those skilled in the art likely would use. In addition, some of the steps may be performed in a different order than that shown. Additionally, or alternatively, some of the steps may be performed at the same time. Furthermore, some embodiments may skip some of these steps. Those skilled in the art therefore can modify the process as appropriate.

The process begins at step 402, which provides a UVC reflective sheet. The sheet may be formed from a UVC reflective material, or it may have UVC reflective material deposited therein. In various embodiments, the sheet may be formed or made to be UVC diffusive or UVC reflective. For example, the sheet may be formed from an inexpensive material that is about 70% reflective to UVC, such as aluminum. This advantageously reduces costs relative to highly UVC reflective material, but require the introduction of a larger fluence of UVC radiation compared to higher UVC reflective material, all else being the same. Additionally, or alternatively, the walls 18 and/or 40 may be coated with a highly UVC reflective material, such as PTFE, to reduce the requirements of UVC fluence in the chamber 12.

One of skill in the art may manipulate the various reflectivity in view of cost factors to achieve a desired outcome. In various embodiments, the sheet may be between 0.5 meters to 5 meters long. Accordingly, illustrative embodiments provide an elongated chamber 12.

The process then proceeds to step 404, which stamps or cuts apertures into the sheet. The apertures are made so that LED radiation 32 may be emitted into the chamber 12. Thus, in some embodiments, the apertures may be sized for the LED chip 26, package 28, and/or light pipe 38, based on how the LED 24 is coupled to the chamber 12. As mentioned previously, the apertures tend to be a UVC absorber, and therefore, are preferably made small.

For example, in various embodiments, the aperture area is smaller than a perimeter the package 28. The package may approximately 5 mm long and/or 5 mm wide. However, in some other embodiments, the aperture may have an area smaller than the chip top surface area. In illustrative embodiments, the chip top surface area is defined by a perimeter having a width of less than about 1 mm, and a length of less than about 1 mm. The aperture may have a width of less than about 1 mm, and/or a length of less than about 1 mm.

Furthermore, in preferred embodiments, the apertures may be made in the sheet such that the LEDs 24 are perpendicular to the flow path and/or so that the LEDs 24 do not directly face one another when the sheet is closed (e.g., rolled up, folded into a rectangular chamber 12, etc.). In some embodiments, step 404 may be skipped, for example, when the LEDs 24 are adhesively attached to the sheet.

At step 406, the LEDs 24 are positioned into the aperture so that light may pass through the aperture. Accordingly, the LEDs may be positioned into the aperture (e.g., the chip 26, the package 28, the entire LED 24, and/or the light pipe 39). At step 408, optical coupler 30 is applied to the LEDs 24. Particularly, the optical coupler is applied to a light emitting surface of the chip 26.

At step 410, the reflective sheet is formed into the sidewall 18 of the chamber 12. Accordingly, the reflective sheet may be rolled to become the sidewall 18 of a cylindrical chamber 12, or it may be folded into a polygonal shaped sidewall 18. For the sake of convenience, illustrative embodiments may refer to a cylinder, but it should be understood that other shapes may easily be used in place of the cylinder, and that the cylinder is not intended to limit various embodiments of the invention. A rolled cylinder is one convenient manufacturing method.

The process proceeds to step 412, which secures the cylinder within an outer housing. The outer housing may include the inlet 14, the outlet 16, and one or more filters 36. The outer housing may also include a printed circuit board for the LEDs 24 (e.g., a flexible PCB). Furthermore, the housing may include heat sinks on which the LEDs 24 may be mounted.

At step 414, the LEDs 24 are coupled to a power source (not shown). The power source allows for the activation and de-activation of the LEDs 24. Finally, at step 416, the LEDs 24 are used to disinfect air that comes into the chamber 12.

Figure 5:
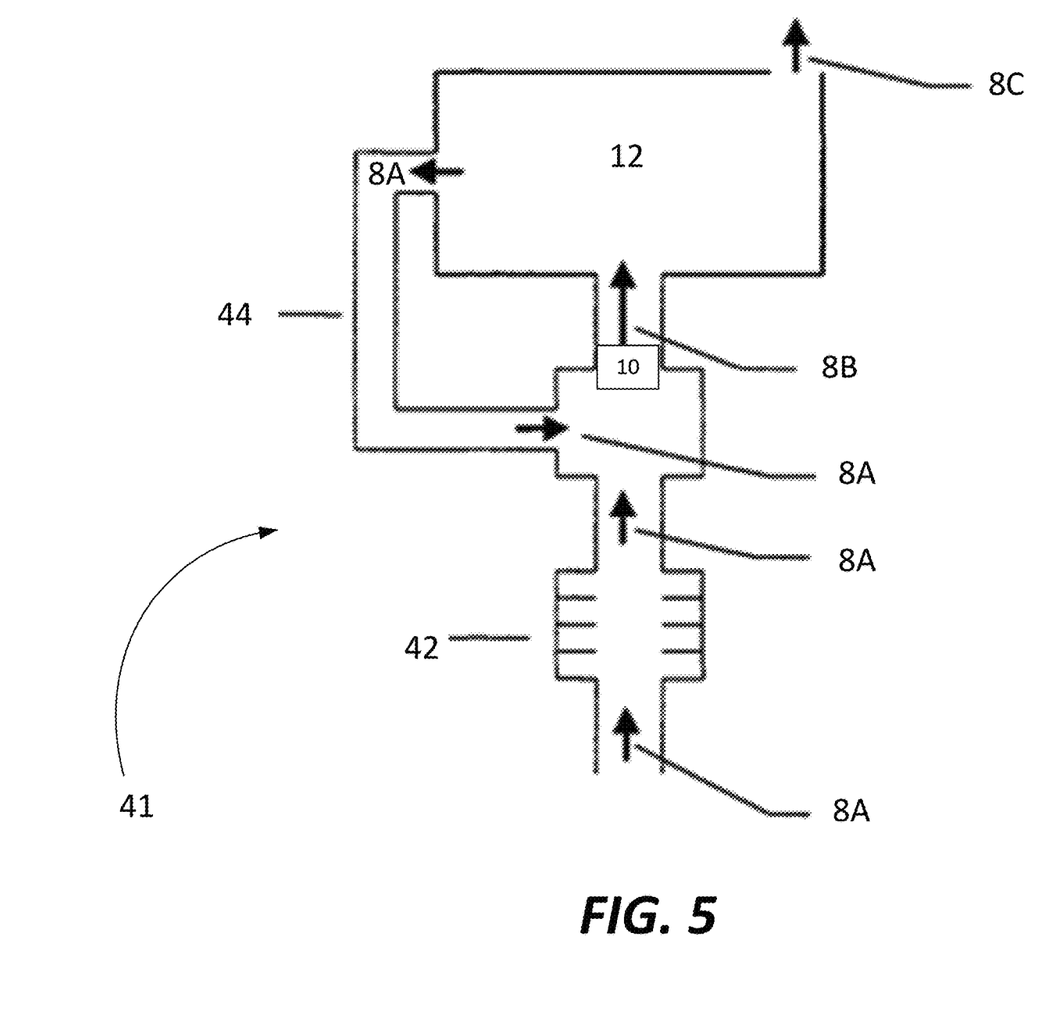
FIG. 5 schematically shows a diagram of the reactor coupled with an environmental control system of an aircraft, in accordance with illustrative embodiments of the invention.

FIG. 5 schematically shows a diagram of the reactor 10 fluidly coupled with an environmental control system 41 of the aircraft 4, in accordance with illustrative embodiments of the invention. In some embodiments, the reactor 10, and thus the chamber 12, may be mounted downstream of an aircraft AC system 42, so that the cold air 8A cools the LEDs 24 in the reactor 10.

Air 8A from the cabin 12 may be recirculated via recirculation channel 44 prior to being passed through the reactor 10, and coming out as disinfected air 8B. In a similar manner, air 8A from outside of the aircraft 4 may enter the AC system 42, and then make its way through the reactor 10. As shown in FIG. 6, some of the disinfected air 8B goes into the cabin and is again recirculated as air 8A. However, some other portion of the air 8C may be removed from the aircraft 4.

Although the above discussion discloses various exemplary embodiments of the invention, it should be apparent that those skilled in the art can make various modifications that will achieve some of the advantages of the invention without departing from the true scope of the invention.

What is claimed is:

1. A method of forming an air disinfection chamber comprising:
   providing a sheet of UVC reflective material wherein the material is at least 90% UVC reflective and diffusively reflective to UVC;
   cutting holes in the UVC reflective material prior to forming the sheet into a cylindrical shape, the holes configured to allow UVC radiation to pass therethrough;
   positioning a respective LED in a respective cut hole; and
   forming the sheet into a cylindrical shape that defines a chamber having a length of about 0.5 meters to about 2 meters.

2. The method as defined by claim 1, further comprising:
   positioning a UVC reflective and UVC transmissive filter in the chamber.

3. The method as defined by claim 2, wherein the filter is positioned adjacent to an inlet of the chamber.

4. The method as defined by claim 2, wherein the filter and/or the sheet is formed from PTFE.

5. The method as defined by claim 1, further comprising flowing air through the chamber.

6. The method as defined by claim 5, wherein air flow into the chamber is increased using a fan upstream of the chamber.

7. The method as defined by claim 1, further comprising emitting radiation into the chamber from at least one LED.

8. The method as defined by claim 2, further comprising positioning an LED to emit radiation towards the filter.

9. The method of claim 1, further comprising applying an optical coupler to the respective LED.

10. The method of claim 1, further comprising fluidly coupling the chamber with an environmental control system of an aircraft.

11. A method of forming an air disinfection chamber comprising:
    providing a sheet of UVC reflective material;
    cutting holes in the UVC reflective material prior to forming the sheet into a cylindrical shape, the holes configured to allow UVC radiation to pass therethrough;
    positioning a respective LED in a respective cut hole;
    forming the sheet into a cylindrical shape that defines a chamber having a length of about 0.5 meters to about 2 meters; and
    coupling a UVC durable and UVC transmissive filter to an inlet of the chamber.

12. The method of claim 11, wherein the chamber has a length of greater than 0.5 meters.

13. The method of claim 12, wherein the chamber has a length of less than 2 meters.

14. The method of claim 11, wherein a fluence rate within the chamber is configured to be greater than about 1 mJ/cm$^2$.

15. The method of claim 11, wherein the filter is positioned immediately adjacent to the inlet.

16. The method of claim 15, further comprising a second filter within the chamber.

17. The method of claim 11, wherein the filter includes an LED embedded therein.

18. The method of claim 11, wherein an LED is positioned to emit light substantially towards the filter.

19. The method of claim 11, further comprising applying an optical coupler to the respective LED.

20. The method of claim 11, further comprising fluidly coupling the chamber with an environmental control system of an aircraft.

* * * * *